(12) United States Patent
Kowalczyk et al.

(10) Patent No.: US 6,936,588 B2
(45) Date of Patent: Aug. 30, 2005

(54) METHOD OF PRODUCTION OF AN ISOMALTULOSE-CONTAINING ENTERAL NUTRIENT

(75) Inventors: Jörg Kowalczyk, Eisenberg/Steinborn (DE); Gunhild Kozianowski, Grünstadt (DE); Markwart Kunz, Worms (DE); Matthias Moser, Grünstadt (DE)

(73) Assignee: Südzucker Aktiengesellschaft Mannheim/Ochsenfurt, Mannheim (DE)

( * ) Notice: Subject to any disclaimer, the term of this patent is extended or adjusted under 35 U.S.C. 154(b) by 0 days.

(21) Appl. No.: 10/682,455

(22) Filed: Oct. 10, 2003

(65) Prior Publication Data

US 2004/0132670 A1 Jul. 8, 2004

(30) Foreign Application Priority Data

Oct. 17, 2002 (DE) ......................................... 102 48 515
Oct. 30, 2002 (DE) ......................................... 102 51 648
Mar. 12, 2003 (DE) ......................................... 103 10 648

(51) Int. Cl.$^7$ ........................... A61K 31/70; C07H 3/04

(52) U.S. Cl. ...................... 514/23; 514/53; 536/123.13; 536/124; 536/18.5; 536/18.6; 536/4.1

(58) Field of Search ................. 514/23, 53; 536/123.13, 536/124, 18.5, 18.6, 4.1

(56) References Cited

U.S. PATENT DOCUMENTS

| 4,948,616 A | 8/1990 | Iijima et al. |
| 4,959,350 A | 9/1990 | Frokjaer et al. |
| 5,741,243 A | 4/1998 | Geckle et al. |
| 2001/0005524 A1 | 6/2001 | Hussein |

FOREIGN PATENT DOCUMENTS

| WO | WO 95/18618 | 7/1995 |

OTHER PUBLICATIONS

Nishio et al. (JP 01191646 A), Aug. 1, 1989 (Abstract Sent).*
Abstract of Okuda et al., Endocrinologia Japonica, vol. 32, No. 6, pp. 933–936 (1985).
Abstract of Crittenden et al., Trends in Food Science & Technology, vol. 7, No. 11, pp. 353–361 (1996).
Singh et al., Journal of Food Science and Technology, India, vol. 12, No. 4, pp. 170–172 (1975).
Grosch Belitz, "Food Chemistry", Springer, Berlin XP 002263917, pp. 488–489.
Deutsche Forschungsanstalt Für Lebensmittelchemie, Wissenschaftliche Verlagsgesellschaft MBH, Stuttgart, Germany, XP 002263918, p. 24 (1991).
Rufian–Henares, et al., "Maillard Reaction in Enteral Formula Processing: Furosine, Loss of o–Phthaldialdehyde Reactivity, and Fluorescence"; Food Research International vol. 35, pp. 527–533 (2002).
Frias, et al., "Stability of Thiamine and Vitamins E and A During Storage of Enteral Feeding Formula", J. Agric. Food Chem., vol. 49, pp. 2313–2317 (2001).
Lowry, et al., "Effect of Storage, Carbohydrate Composition, and Heat Processing on Protein Quality and Amino Acid Bioavailability of a Commercial Enteral Product", Journal of Food Science, vol. 54, No. 4, pp. 1024–1030 (1989).
Wallhausser, Desinfelktion–Konservierun (1995), sections 4.2.1.2.1 and 4.2.1.2.2 (with English translation).
Abstract of Japanese Application No. JP 10–179036 (Jul. 7, 1998).

* cited by examiner

*Primary Examiner*—Elvis Q. Price
*Assistant Examiner*—Michael C. Henry
(74) *Attorney, Agent, or Firm*—Dickstein, Shapiro, Morin & Oshinsky, L.L.P.

(57) ABSTRACT

The present invention relates to a method for the production and use of enteral nutrients, particularly an enteral solution, wherein this method is distinguished by a particularly gentle processing, particularly of the carbohydrate components contained in the solution.

20 Claims, No Drawings

METHOD OF PRODUCTION OF AN ISOMALTULOSE-CONTAINING ENTERAL NUTRIENT

FIELD OF THE INVENTION

The present invention relates to a method of production and use of an enteral nutrient, in particular an enteral solution or suspension.

BACKGROUND OF THE INVENTION

An enteral nutrient is a nutrient which is supplied either orally or gastrointestinally to a patient or consumer without decomposition of the nutrient taking place in the user's mouth or pharynx. Because of this, enteral nutrients are as a rule in the form of solutions or suspensions, and are used in both humans and animals. Complete enteral nutrients usually contain fat, carbohydrate and protein components and frequently also additives, for example, for increasing their stability or improving flavor. Their production as a rule includes pasteurization, homogenization, and sterilization steps using high temperatures and pressures.

BRIEF SUMMARY OF THE INVENTION

A complete enteral nutrient is known from U.S. Pat. No. 4,497,800. The enteral solution described there has a low pH value and consequently is microbially quite stable. However, the very high osmolality, and the necessity of adding emulsifiers, are a disadvantage.

A further enteral nutrient is known from EP 0 126 666, but nevertheless is characterized by a bitter taste.

From U.S. Pat. No. 4,959,350, a liquid enteral nutrient is known, likewise with a low pH value, and distinguished by an improved taste. To obtain microbial stability, the solution was pasteurized at 85° C. for 4 seconds.

Common to the above-mentioned nutrients is that these are open to improvement from the nutrition physiological standpoint. Thus as a rule they contain glycemic carbohydrates which lead to a rapid and high blood glucose level and have a high insulin requirement which burdens the metabolism. Alternative carbohydrates such as fructose, on the other hand, supply no nutrition-physiologically useful glucose and decompose during the production of the nutrient solutions. In addition, the known methods for the production of enteral solutions frequently lead to decomposition of components, particularly ketoses, present in the enteral nutrient, due to the process conditions used for pasteurization and sterilization. The patient consequently receives on the one hand too little of the components concerned, particularly ketoses, and on the other hand too much of conversion products, for example, products of the Maillard reaction such as AGEs (Advanced Glycation End-products).

DETAILED DESCRIPTION OF THE INVENTION

The present invention is therefore based on the technical problem of providing a method for the production of an enteral nutrient, particularly ketose-containing enteral solution or suspension, which overcomes the said disadvantages and in particular leads to a technically simple and inexpensive preparation of a germ-free or germ-reduced enteral nutrient which is particularly valuable from the nutrition physiological standpoint, is low glycemic, and nevertheless provides glucose.

The present invention overcomes the technical problem on which it is based by the provision of a method for the production of an isomaltulose-containing enteral nutrient, in particular an enteral solution or suspension, comprising the steps of (a) provision of the starting components: water, fat, at least one nitrogen-containing component, and at least one carbohydrate-containing component, particularly isomaltulose, (b) subsequent homogenization of the starting components provided, and (c) subsequent pasteurization of the starting components for 10–30 seconds at temperatures $\geq 135°$ C., preferably 135–137° C. The order of steps (b) and (c) can of course be interchanged, that is, in such an embodiment the method relates to a method with the sequence (a) provision of the starting components, (c) pasteurization of the provided components under the said conditions, and (b) subsequent homogenization of the pasteurized starting components.

The present invention also overcomes the technical problem on which it is based by the provision of a method for the production of an isomaltulose-containing enteral nutrient, in particular an enteral solution or enteral suspension, comprising the steps of (a') provision of the starting components: water, fat, at least one nitrogen-containing component, and at least one carbohydrate-containing component, particularly isomaltulose, (b') subsequent homogenization of the starting components provided, and (c') subsequent sterilization, particularly autoclaving, of the starting components for 5–15 minutes at temperatures $\geq 120°$ C., preferably 125–128° C. The order of steps (b') and (c') can of course be interchanged, that is, in such an embodiment the method relates to a method with the sequence (a') provision of the starting components, (c') sterilization of the provided components under the said conditions, and (b') subsequent homogenization of the autoclaved starting components.

In a further embodiment, the invention relates to a method with the said steps (a), (b), and (c), or (a), (c), and (b), wherein in addition to the last method step of the said method, if necessary with the addition of additional materials, sterilization is performed, particularly autoclaving of the homogenized and pasteurized starting components, preferably autoclaving at temperatures $\geq 120°$ C., preferably 125–128° C., for a period of 5–15 minutes.

In a further preferred embodiment, it is provided that the said pasteurizing step and/or the said sterilization step are performed at a pH value of 6.5–8.0, preferably 6.5–7.5. In a preferred embodiment, it can be provided that the adjustment of the pH value takes place at the beginning of, or during, the said production method.

In connection with the present invention, "enteral nutrient" is in particular understood to mean a germ-reduced, substantially germ-free or low-germ, enteral solution or enteral suspension which is suitable for the peroral or gastrointestinal (probe feeding) nutrition of the human or animal body. "Germs" are microbial organisms, or reproductive products of such organisms, particularly fungi, spores, yeasts, bacteria, bacilli, protozoa, algae, lichens, cyano-bacteria, etc. In connection with the present invention, by "pasteurizing" is understood a killing brought about by heat of special kinds of germs and viruses, complete freedom from germs and viruses not being attained. By "sterilization", particularly autoclaving which is sterilization in a steam pressure vessel, is understood a process directed to the complete killing of germs and viruses, which in particular according to the invention uses heating to at least 120° C.

The invention thus envisages the provision of an enteral nutrient which contains isomaltulose (also termed palatinose) as the carbohydrate, besides the water, fat, and nitrogen-containing components required for complete nutrition. Isomaltulose provides nutrition-physiologically favorable glucose by slow liberation, without burdening the metabolism with high insulin requirement. Isomaltulose is thus found to be particularly advantageous for the enteral nutrient produced and used according to the invention because of its slow glucose liberation and its insulin-independent metabolism with full energy value. Furthermore, the production and use according to the invention are distinguished by a reduced content of AGEs. In a preferred embodiment of the present invention, no carbohydrate other than isomaltulose is present in the enteral nutrient, particularly no further sugar. Isomaltulose in this embodiment is the one and only carbohydrate, particularly the only sugar, in the enteral nutrient. In a further preferred embodiment, it can however be provided that isomaltulose is present together with other carbohydrates, for example, glucose, fructose, invert sugar, lactose, maltose, trehalose, maltodextrin, pectin, saccharose, starches, hydrolyzed starches, or sugar conversion materials such as isomaltol or other sugar alcohols such as lycasin, mannitol, sorbitol, xylitol, erythritol, maltitol, lactitol, 1,6-GPS (6-O-α-D-glucopyranosyl-D-sorbitol), 1,1-GPM (1-O-α-D-glucopyranosyl-D-mannitol, or 1,1-GPS (1-O-α-D-glucopyranosyl-D-sorbitol), etc. In the last-named embodiment, it is particularly preferably provided according to the invention that the isomaltulose replaces a portion of the carbohydrate usually present in a commercially obtainable enteral nutrient, in particular, replaces $\geq 30$, $\geq 40$, $\geq 50$, $\geq 60$, $\geq 70$, $\geq 80$, $\geq 90$, or $\geq 95$ wt.-% (based on dry substance of all carbohydrates in the enteral nutrient).

The invention particularly provides for the use as the carbohydrate, isomaltulose alone or in substantial proportions in the enteral nutrient, and to pasteurize the isomaltulose-containing starting components for 10–30 seconds at temperatures of at least 135° C., particularly 135–137° C., and/or to sterilize the isomaltulose-containing starting components for 5–15 min. at temperatures of at least 120° C., particularly at 125–128° C. A reduction of carbohydrate decomposition can usually be attained by lower temperatures. It has surprisingly been found that a reduction of the ketose decomposition can be achieved, even at high temperatures, by reducing the residence time. By maintaining this recipe and pasteurizing conditions, a particularly high isomaltulose content in the homogenized, ready for use enteral nutrient is surprisingly obtained. The enteral nutrient obtained gently in this manner, nevertheless germ-free or germ-reduced, is distinguished in a particularly advantageous manner by high storage stability, high microbial stability, and good organoleptic properties, and has a pleasant, sweet taste. Furthermore, isomaltulose is split by the glucosidases of the small intestinal wall only in a delayed manner. In comparison with the rapidly digestible carbohydrates, this results in a slow rise of blood glucose. The released fructose is simultaneously reabsorbed. Both together lead to isomaltulose requiring hardly any insulin for metabolism, differing from the rapidly digestible, highly glycemic foodstuffs. Moreover, isomaltulose is particularly suitable, because of the delayed decomposition in the small intestine, for maintaining oxidative metabolism. The present enteral nutrient is thus outstandingly suitable as a "slow release" nutrition, i.e., nutrition with delayed, continuous carbohydrate liberation, which at the same time is suitable, because of the low insulin requirement, for persons suffering from disturbances of blood glucose metabolism.

In a further preferred embodiment of the invention, as mentioned, following on the last step of the production method according to the invention, that is, after the pasteurizing or homogenizing step (b) or (c), a step of sterilizing the homogenized starting components is performed. As long as the obtained enteral solution is filled after pasteurizing into sterile containers, this sterilizing step can be dispensed with.

It can also be provided according to the invention to dry the product after pasteurizing, homogenizing, or sterilizing, particularly autoclaving, in particular to spray dry it and possibly to agglomerate it. The powder obtained is reconstituted before use by dissolving in water.

The invention therefore relates to the isomaltulose-containing enteral nutrients produced by means of the method described in the present technical teaching.

In a preferred embodiment of the invention, this relates to an enteral nutrient with 70–80 wt.-% water (based on the total weight of the whole solution or suspension).

In a further preferred embodiment of the present invention, this relates to an enteral nutrient with 1–3.5 wt.-% nitrogen-containing components (based on the total weight of the enteral nutrient).

In a further preferred embodiment of the present invention, this relates to an enteral nutrient with 2–4.5 wt.-% fat (based on the total weight of the enteral nutrient).

In a further preferred embodiment of the present invention, this relates to an enteral nutrient with 6–11 wt.-% carbohydrate (based on the total weight of the enteral nutrient). In a preferred embodiment, the isomaltulose content is 1–20 wt.-%, preferably 5–15 wt.-% (based on the total weight of the solution or suspension).

In a further preferred embodiment of the present invention, the enteral nutrient, in particular the enteral solution, has a pH value of 2–10, particularly 2–8, preferably 6.5–8.0, more preferably 6.5–7.5.

In a further preferred embodiment of the present invention, (in relation to the total energy content), the fat content, particularly triglycerides, is 3–60%, the content of nitrogen-containing components is 10–35%, and the carbohydrate content is 5–87%.

In a particularly preferred embodiment, the osmolality is equal to or less than 350 milliosmal.

In a particularly preferred embodiment of the present invention, the fat used is a vegetable fat, particularly a vegetable oil, for example, corn oil, coconut oil, soy oil or sunflower oil, or mixtures thereof. It is of course also possible to use other fat components, particularly synthetic oils.

In a further preferred embodiment, used as the nitrogen-containing component are proteins, peptides, amino acids, mixtures thereof, protein or peptide hydrolysates, particularly hydrolyzed lactalbumin, hydrolyzed milk, acid milk, casein, hydrolyzed casein, caseinates, hydrolyzed soy bean protein, and/or free amino acids. In a preferred embodiment, nitrogen-containing components are used which represent proteins of vegetable origin or are produced therefrom. According to the invention, there can for example be used protein hydrolysates from colza, beans, wheat, sesame or peas. Mixtures of such hydrolysates can of course be used.

In a further preferred embodiment, it is provided that the starting components of step (a) also include flavorants, buffers, salts, preservatives, odorants, further sweeteners, minerals, vitamins, inert materials, acids compatible with foodstuffs, trace elements, electrolytes and/or emulsifiers, pharmacologically active materials, antibiotics, antioxidants, etc.

The invention also relates to the use of isomaltulose in enteral nutrients or for the production of enteral nutrients, preferably produced according to one of the abovementioned methods, as a low-glycemic carbohydrate, that is, with low insulin requirement, the enteral nutrient being suitable for healthy human or animal bodies or for human or animal bodies with disturbed glucose and/or insulin metabolism.

Further advantageous embodiments of the present invention will become apparent from the dependent claims.

The invention will be described in detail using the following examples.

EXAMPLE 1

Production and Pasteurizing an Enteral Solution with Palatinose Addition (by UHT (Ultra High Temperature))

(A) The solution components according to the following recipe (Section B) are taken up in water in a glass beaker in the sequence salts, vitamins, carbohydrates and finally proteins and are homogenized using an ultra Turrax stirrer. The homogenized mass is then forwarded through the trial plant by means of a pump. The trial plant consists of the sections inlet, preheater, UHT heater, heat retainer, cooler and outlet. The UHT heater is indirectly heated with steam, as usually used for the UHT heating of milk. The residence time in the heat retainer system is varied by means of the pump delivery. The pasteurization according to the invention is performed according to the trial times and temperatures given in the following Table 1.

The analytical data of the carbohydrate components are obtained by high performance anion exchange chromatography (HPAEC) with NaOH as eluent and amperometric detection.

TABLE 1

|  | Batch 1 | Batch 2 | Batch 3 |
|---|---|---|---|
| T (Temperature) [° C.] | 130 | 135 | 140 |
| T (time) [sec.] | 50 | 30 | 10 |
|  | (control) |  |  |
| Isomaltulose [g/kg] |  |  |  |
| Solution before UHT step | 101.07 | 100.23 | 100.07 |
| Solution after UHT step | 69.25 | 72.52 | 81.20 |
| Isomaltulose decomposition [%] | 31 | 28 | 19 |

The germ and virus numbers obtained were substantially identical in all three trials. However, the isomaltulose decomposition was markedly reduced in the method according to the invention (Batches 2 and 3) in contrast to a control batch with reduced temperature and longer pasteurizing time. A reduction of decomposition by about a third resulted from the shortening of the incubation times.

(B) Example of Recipe with Isomaltulose

| Raw Material | Kg/100 kg |
|---|---|
| Water | 76.379001 |
| Isomaltulose | 10.000000 |
| Glucidex 12 maltodextrin 10 DE | 5.295000 |
| Calcium caseinate, spray dried | 3.400000 |
| Fat mixture, standard | 3.110000 |
| Sodium caseinate, spray-dried | 0.900000 |
| Potassium chloride | 0.185500 |
| Emulsifier, Myverol 18-0, as monoglyceride | 0.125000 |
| Tripotassium citrate monohydrate | 0.110000 |
| Potassium dihydrogen phosphate, K11-01 | 0.105000 |
| Emulsifier, Halocithin 02-F | 0.080000 |

-continued (B) Example of Recipe with Isomaltulose

| Raw Material | Kg/100 kg |
|---|---|
| Trisodium citrate dehydrate, grade 6090 | 0.080000 |
| Tricalcium phosphate | 0.060000 |
| Glucidex 21 Maltodextrin 20 DE | 0.044122 |
| Magnesium oxide, heavy | 0.040000 |
| Potassium dihydrocitrate, anhydrous | 0.030000 |
| Choline bitartrate, coated | 0.022000 |
| Vitamin C, pulverized | 0.013600 |
| Iron-II lactate | 0.005000 |
| Zinc sulfate monohydrate | 0.002750 |
| Sodium chloride | 0.002000 |
| Nicotinamide | 0.002000 |
| Antioxidant, ascorbyl palmitate | 0.001500 |
| Vitamin A acetate 325 | 0.001400 |
| Potassium iodide, 1% I trituration | 0.001150 |
| Cu-II gluconate | 0.000845 |
| Mn-II sulfate monohydrate | 0.000715 |
| Ca D-pantothenate | 0.000550 |
| Sodium molybdate, 1% molybdenum trituration | 0.000500 |
| Vitamin D3 | 0.000450 |
| Sodium fluoride | 0.000400 |
| Sodium selenide 1% selenium trituration | 0.000300 |
| Vitamin B12 0.1% | 0.000240 |
| Chromium-III chloride, 1% chromium trituration | 0.000225 |
| Vitamin B6 HCl | 0.000225 |
| Vitamin B2 | 0.000187 |
| Vitamin B1 HCl | 0.000150 |
| Vitamin K1 5% SD | 0.000060 |
| Folic acid | 0.000024 |
| Biotin, d | 0.000006 |
| Total | 100.000000 |

EXAMPLE 2

Sterilization by Autoclaving

The solution components according to the recipe of Example 1 (Section B) are received in water in a glass beaker in the sequence salts, vitamins, carbohydrates and finally proteins and were homogenized by means of an ultra Turrax stirrer. The homogenized mass is then transferred to an autoclave and sterilized in a laboratory steam autoclave. According to this description, the autoclaving (sterilization) according to the invention is performed with the trial times and temperatures as given in the following Table 2.

The analytical data for the carbohydrate constituents were obtained by high performance anion exchange chromatography (HPAEC) with NaOH as the eluent and amperometric detection.

TABLE 2

Results:

|  | Batch 1 | Batch 2 | Batch 3 |
|---|---|---|---|
| T (Temperature) [° C.] | 115 | 121 | 128 |
| T (time) [sec.] | 30 | 15 | 5 |
| P (bar$_{abs}$) | 1.7 | 2.1 | 2.5 |
|  | (control) |  |  |
| Isomaltulose [g/kg] |  |  |  |
| Solution before autoclaving | 100.25 | 100.13 | 100.26 |
| Solution after autoclaving | 58.71 | 61.27 | 69.37 |
| Isomaltulose decomposition [%] | 41 | 39 | 31 |

The germ and virus numbers obtained were substantially identical in all three trials. However, the isomaltulose decomposition was markedly reduced in the method according to the invention (Batches 2 and 3) in contrast to a control batch with reduced temperature and longer sterilization time. A reduction of decomposition by about 33% resulted from the shortening of the incubation times.

EXAMPLE 3

Production, Pasteurizing (UHT Heating) and Sterilizing (Autoclaving) of an Enteral Solution with Palatinose Addition The solution components according to the recipe of Example 1 (Section B) are taken up in water in a glass beaker in the sequence salts, vitamins, carbohydrates and finally proteins and are homogenized using an ultra Turrax stirrer. The homogenized mass is then forwarded through the trial plant by means of a pump. The trial plant consists of the sections inlet, preheater, UHT heater, heat retainer, cooler and outlet. The UHT heater is indirectly heated with steam, as usually used for the UHT heating of milk. The residence time in the heat retainer system is varied by means of the pump delivery. The pasteurization according to the invention is performed according to the trial times and temperatures given in the following Table 3.

The analytical data of the carbohydrate components were obtained by high performance anion exchange chromatography (HPAEC) with NaOH as eluent and amperometric detection.

TABLE 3

| Results: | | | |
|---|---|---|---|
| | Batch 1 | Batch 2 | Batch 3 |
| T (Temperature) [° C.] | 130 | 135 | 140 |
| T (time) [sec.] | 50 (Control) | 30 | 10 |
| Isomaltulose [g/kg] | | | |
| Solution before UHT step | 100.65 | 99.38 | 100.05 |
| Solution after UHT step | 66.38 | 76.36 | 83.72 |
| Isomaltulose decomposition [%] | 34 | 23 | 16 |

The product of reaction batch 3 (i.e., the product with the highest residual isomaltulose fraction after the pasteurizing step) is transferred to an autoclave and sterilized in a laboratory steam autoclave. According to this description, the autoclaving (sterilization) is performed with the trial times and temperatures given in the following Table 4.

The analytical data of the carbohydrate components were obtained by high performance anion exchange chromatography (HPAEC) with NaOH as eluent and amperometric detection.

The germ and virus numbers obtained were substantially identical in all three trials. However, the isomaltulose decomposition was markedly reduced in the method according to the invention (Batches 2 and 3, 5 and 6) in contrast to the control batches with reduced temperature and longer sterilization time. A reduction of decomposition of about a 40% for the autoclaving step and of 22% for the overall process resulted from the shortening of the incubation times.

TABLE 4

| Results: | | | |
|---|---|---|---|
| | Batch 4 | Batch 5 | Batch 6 |
| T (Temperature) [° C.] | 115 | 121 | 128 |
| T (time) [sec.] | 30 | 15 | 5 |
| P (bar$_{abs}$) | 1.7 (control) | 2.1 | 2.5 |

TABLE 4-continued

| Results: | | | |
|---|---|---|---|
| | Batch 4 | Batch 5 | Batch 6 |
| Isomaltulose [g/kg] | | | |
| Solution before autoclaving | 83.72 | 83.72 | 83.72 |
| Solution after autoclaving | 60.28 | 65.30 | 70.20 |
| Isomaltulose during autoclaving [%] | 28 | 22 | 16 |
| Isomaltulose decomposition [%] | 40 | 35 | 31 |

What is claimed is:

1. Method of production of an isomaltulose-containing enteral nutrient comprising subjecting starting components comprising water, fat, at least one nitrogen-containing component, and carbohydrate with the inclusion of isomaltulose to the following steps in any order:

homogenization, and a least one of (a) pasteurizing the starting components for 10–30 seconds at temperature $\geq 135°$ C., and (b) sterilizing the starting components.

2. Method of production of an isomaltulose-containing enteral nutrient according to claim 1 wherein the sterilizing is effected by autoclaving the starting components for 5–15 min. at temperatures $\geq 120°$ C.

3. Method according to claim 1, wherein homogenized and pasteurized starting components are sterilized.

4. Method according to claim 1, wherein the pasteurizing temperature is 135–137° C.

5. Method according to claim 1, wherein the sterilizing is effected by autoclaving at 125–128° C.

6. Method according to claim 1, wherein the pasteurizing or the sterilizing or both take place at a pH value of 6.5–8.0,.

7. Method according to claim 1, wherein the nutrient is a liquid.

8. Method according to claim 1, wherein the nitrogen-containing component is at least one protein, at least one peptide, at least one amino acid, a mixture of amino acids, or a protein or peptide hydrolysate, or a mixture of at least two of the said components.

9. Method according to claim 1, wherein the nitrogen-containing component is soy bean protein hydrolysate, casienate, hydrolyzed casein, casein hydrolyzed whey protein, hydrolyzed lactalbumin, or a mixture thereof.

10. Method according to claim 1, wherein the fat is present in the form of vegetable fat.

11. Method according to claim 1, wherein the fat is corn oil, coconut oil, sunflower oil, soy oil, or a mixture thereof.

12. Method according to claim 1, wherein besides isomaltulose, said carbohydrate is selected from group consisting of maltodextrin, saccharose, glucose, fructose, trehalose, invert sugar, lactose, lactitol, maltitol, erythritol, xylitol, mannitol, sorbitol, lycasin, isomaltol, maltose, pectin, starches, hydrolyzed starches, or a mixture thereof.

13. Method according to claim 1, wherein the isomaltulose is the single carbohydrate in the enteral nutrient.

14. Method according to claim 1, wherein the pasteurizing or the sterilizing or both take place at a pH value of 6.5–7.5.

15. Method according to claim 1, wherein the nutrient is in the form of a solution or suspension.

16. Method according to claim 1, wherein the fat is present in the form of vegetable oil.

17. Method according to claim 1, wherein homogenized and sterilized starting components are pasteurized.

18. Method according to claim 1, wherein pasteurized and sterilized starting components are homogenized.

19. Method according to claim 7, wherein the pasteurizing or the sterilizing or both take place at a pH value of 6.5–8.0.

20. Method according to claim 1, wherein the nutrient is in the form of a solution or suspension; the nitrogen-containing component is at least one protein, at least one peptide, at least one amino acid, a mixture of amino acids, or a protein or peptide hydrolysate, or a mixture of at least two of the said components; and the fat is present in the form of vegetable fat.

* * * * *